United States Patent [19]

Otten

[11] Patent Number: 5,326,448
[45] Date of Patent: Jul. 5, 1994

[54] METHOD FOR REDUCING THE POLARIZATION OF BIOELECTRICAL STIMULATION LEADS USING SURFACE ENHANCEMENT, AND PRODUCT MADE THEREBY

[75] Inventor: Josephus M. Otten, Miami, Fla.

[73] Assignee: Telectronics Pacing Systems, Inc., Englewood, Colo.

[21] Appl. No.: 961,187

[22] Filed: Oct. 15, 1992

[51] Int. Cl.$^5$ ............................................. G01N 27/26
[52] U.S. Cl. ................................... 204/402; 204/434; 204/140; 204/141.5; 204/153
[58] Field of Search ............ 204/402, 434, 140, 141.5, 204/153

[56] References Cited

U.S. PATENT DOCUMENTS

| | | | |
|---|---|---|---|
| 4,408,604 | 10/1983 | Hirshorn et al. | 128/785 |
| 4,502,492 | 3/1985 | Bornzin | 128/785 |
| 4,542,752 | 9/1985 | De Haan et al. | 128/784 |
| 4,603,704 | 8/1986 | Mund et al. | 128/784 |
| 4,611,604 | 9/1986 | Botvidsson et al. | 128/784 |
| 4,612,100 | 9/1986 | Edeling et al. | 204/192.15 |
| 4,649,937 | 3/1987 | De Haan et al. | 128/784 |
| 4,679,572 | 7/1987 | Baker, Jr. | 128/786 |
| 4,762,136 | 8/1988 | Baker, Jr. | 128/786 |
| 4,786,373 | 11/1988 | Saloheimo et al. | 204/402 |
| 5,167,779 | 12/1993 | Henig | 204/140 |

OTHER PUBLICATIONS

A. Visintin et al., "Growth Modes of Platinum Overlayers Resulting from Square Wave Perturbing Potential Treatments of Different Symmetries", *J. Electroanal. Chem.*, vol. 67, pp. 191–205, (1989).

*Primary Examiner*—John Niebling
*Assistant Examiner*—Bruce F. Bell
*Attorney, Agent, or Firm*—Gottlieb, Rackman and Reisman

[57] ABSTRACT

A method is disclosed for greatly reducing pacing polarization of a porous platinum bioelectrical stimulation electrode substrate by applying an oscillating current to the electrode substrate while it is immersed in an electrolyte such as a sodium sulfate solution to electrochemically cause the formation of a thick, highly porous platinum hydrous oxide surface layer on the substrate. The surface layer is then slowly reduced to platinum, while maintaining an increased surface area structure therein, using a similar electrochemical process employing much lower levels of current. This method does not alter the electrode characteristics other than to increase the microsurface area. The reduced polarization follows from the known inverse relationship between microsurface area and polarization. An electrode made by the foregoing method is also disclosed.

31 Claims, 7 Drawing Sheets

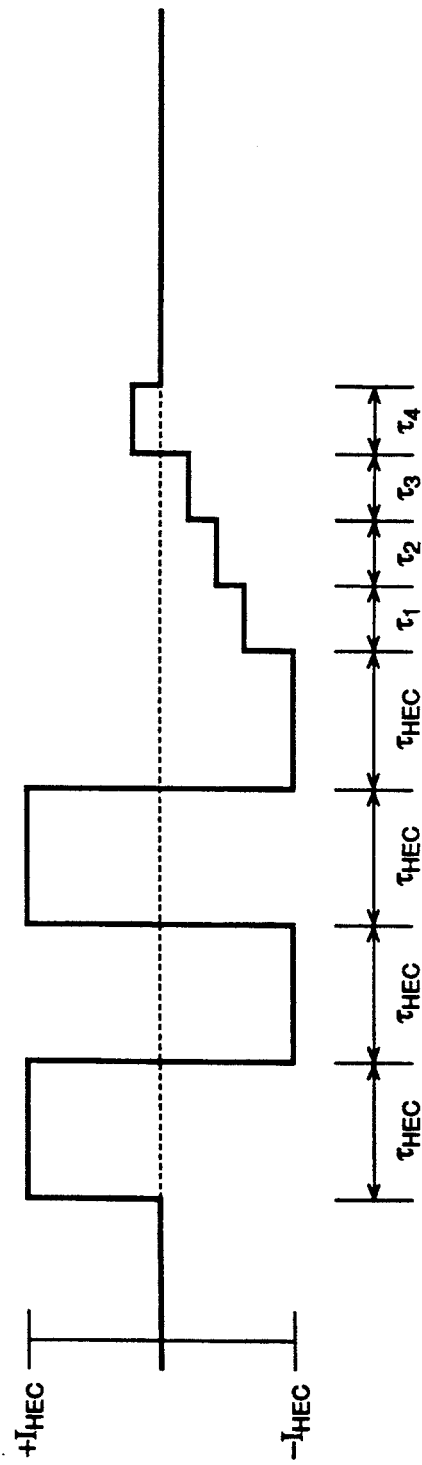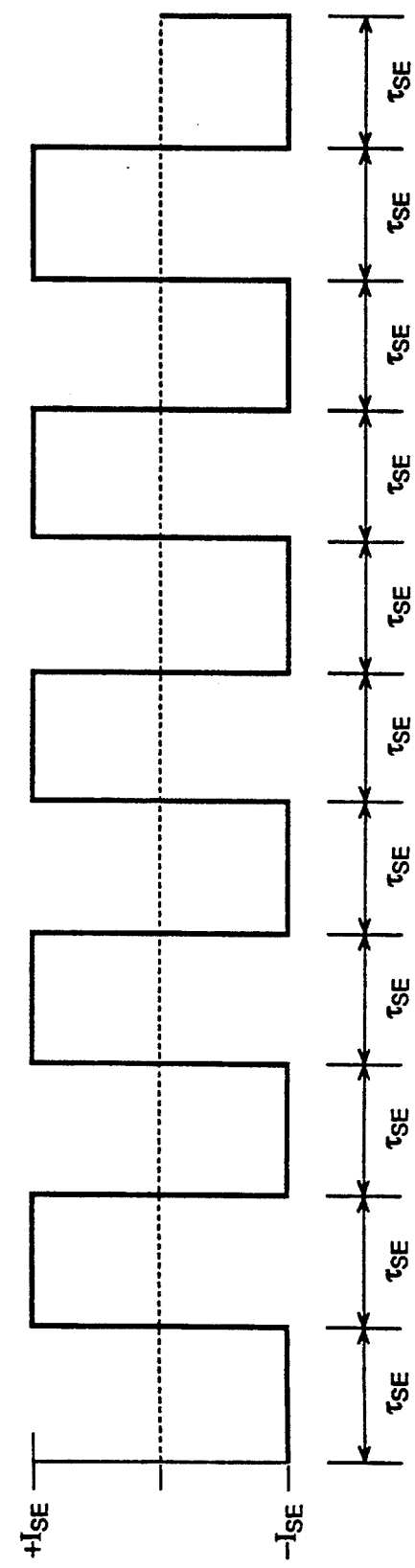

METHOD FOR REDUCING THE POLARIZATION OF BIOELECTRICAL STIMULATION LEADS USING SURFACE ENHANCEMENT, AND PRODUCT MADE THEREBY

FIELD OF THE INVENTION

The present invention relates generally to leads and electrodes for bioelectrical stimulation and bioelectrical signal sensing devices, including cardiac pacemakers and defibrillators, as well as neurostimulators, cardiomyoplasty stimulators and electrophysiology diagnostic and therapeutic devices. More particularly, the present invention relates to low polarization leads and electrodes and a method for treating stimulation leads and electrodes to improve their polarization characteristics for generating electrical stimuli and sensing electrical activity of the heart.

BACKGROUND OF THE INVENTION

Bioelectrical stimulation electrodes may be judged according to many criteria, two of which are biocompatability with tissues in the body and low polarization impedance. Electrochemically, "polarization impedance" is a term which describes the inefficiency of an electrode in transferring energy to or from adjacent body tissues. Polarization impedance is a measure of the energy consumed in electrochemical reactions at the electrode-tissue interface. A low polarization impedance is important for stimulating the heart because a suprathreshold stimulating current can be applied to the heart which causes only slight potential changes. Therefore, electrochemical reactions with the body fluid are suppressed and the energy expenditure required for stimulating the heart is greatly reduced. Furthermore, a low polarization impedance is desirable for sensing intrinsic or natural bioelectrical signals, because for such intrinsic signals only a small measurement current flows and low polarization electrodes reduce the demands made on the input impedance of the sensing amplifiers. The practical result of using low polarization electrodes is to lessen the noise detected during the sensing of a bioelectrical signal. In addition, sophisticated bioelectrical stimulation devices may perform analysis of intrinsic bioelectrical signals and evoked potentials. Low polarization electrodes promote the capability to analyze these signals by abating problems arising from polarization artifact and noise signals, which otherwise could obscure desired physiological signals. Porous platinum electrode surfaces are especially desirable in this regard because of their high degree of biocompatability and their superior electrical properties.

U.S. Pat. No. 4,408,604, entitled "Porous Pacemaker Electrode Tip" granted on Oct. 11, 1983 to M. S. Hirshorn et al. discloses a porous pacemaker electrode tip comprising a concavo-convex electrode cap having a plurality of apertures therethrough and an electrode shaft having a supporting edge formed thereon to which the concave surface of the electrode is joined. The porous cardiac pacemaker electrode is formed by deforming a platinum plate onto a concavo-convex shaped cap member, thereby forming a plurality of selectively spaced apertures through the electrode cap member to make the electrode cap substantially porous.

U.S. Pat. No. 4,502,492, entitled "Low-Polarization Low-Threshold Electrode" granted to G. A. Bornzin on Mar. 5, 1985 teaches a cardiac pacing lead electrode having a low impedance by virtue of a platinum black coating and a novel geometry, involving circular grooves and tines to bring the electrode into contact with the endocardial wall in roughly a perpendicular configuration with respect to the grooves.

U.S. Pat. No. 4,542,752, entitled "Implantable Device having Porous Surface with Carbon Coating", issued Sep. 24, 1985 to A. DeHaan et al. discloses an electrode having the advantage of a low polarization impedance, which is accomplished by means of a porous carbon coating overlying a porous substrate or surface of an implantable device. The procedure for forming this porous carbon coating involves depositing a plasma coating by subjecting the substrate surface to a gaseous environment. This degrades the hydrocarbon in the substrate to form the porous carbon lattice structure.

U.S. Pat. No. 4,603,704, entitled "Electrode for Medical Applications", granted on Aug. 5, 1986 to K. Mund et al. describes a low polarization electrode comprising an electrically conductive carrier material and a porous layer in its active region, which is composed of a carbide, nitride or carbonite of one of the metals titanium, vanadium, zirconium, niobium, molybdenum, hafnium, tantalum or tungsten. The porous layers are applied to the substrate by means of physical vapor deposition.

U.S. Pat. No. 4,611,604, entitled "Bipolar Electrode for Medical Applications" issued to L Bodvidsson et al on Sep. 16, 1986 teaches an electrode with low polarization which is achieved by means of a toughened or porous material surface (e.g. a sintered metal alloy), underlying a layer of activated glassy carbon that has an extremely high double layer capacitance of up to 0.1 $F/cm^2$. The best porous material surface is provided by a layer of a carbide, nitride or carbonitride of at least one of the metals titanium, vanadium, zirconium niobium, molybdenum, hafnium, tantalum or tungsten. The porous carbide, nitride or carbonium layers are situated upon an electrically conductive carrier material, for example platinum, titanium or a metal alloy such as Elgiloy.

U.S. Pat. No. 4,612,100, entitled "Method for the Fabrication of an Implantable Electrode", issued on Sep. 16, 1986 to M. Edeling et al. teaches a procedure for manufacturing an implantable stimulation electrode having a body portion with an outer surface, in which a layer of vitreous carbon is sputtered from a target of vitreous carbon onto at least a portion of the outer surface of the electrode body.

U.S. Pat. No. 4,649,937, entitled "Etched Grooved Electrode for Pacing Lead and Method for Making Same", issued Mar. 17, 1987 to A. DeHaan et al. provides a low impedance electrode having a plurality of grooves etched into the surface of the tip electrode to expand its surface area. The enlarged surface area lessens the polarization of the electrode while maintaining the overall diameter of the electrode so that the large surface area is within a small displaced surface area to ensure an electric current flow which is sufficient to cause muscle depolarization of the heart.

U.S. Pat. No. 4,679,572, entitled "Low Threshold Cardiac Pacing Electrodes", and U.S Pat. No. 4,762,136, entitled "Low Polarization Pacing Electrodes for Capture Verification", issued to R. G. Baker, Jr. on Jul. 14, 1987 and Aug. 9, 1988, respectively, disclose pacing electrodes which achieve low polarization by using an iridium oxide layer overlying the surface of the stimulating cathode.

Each of the aforementioned patents describes low polarization cardiac pacing leads, wherein the low polarization character of the leads is provided by either the application of special coatings to the pacing electrodes or by etching geometrical structures into an electrode. Either alternative increases the complexity of the process of manufacture for a pacing lead and raises the cost of a lead. What is desired is a method for reducing the polarization of a pacing lead that does not require application of a coating to an electrode and does not require painstaking application of solvents, etching solutions and photosensitive solutions which are required in the etching process.

It is known in the field of electrochemistry that the surface of metal electrodes immersed in aqueous solutions can be substantially modified by applying periodic electrical potentials of various waveforms. (For example, see A. Visintin et al., "Growth Modes of Platinum Overlayers Resulting from Square Wave Perturbing Potential Treatments of Different Symmetries", in *J. Electrical Chem.*, Vol. 267, pp. 191-205, 1989.) The surface area of an electrode is electrochemically changed by varying the relative proportion of crystallographic faces through a process of electrochemical faceting and by producing different particular surface morphologies.

The work in the field of electrochemistry generally refers to a method for increasing the surface area of electrodes for usage in electrocatalysis. Heretofore, none of these electrochemical methods are known to have been applied to bioelectrical stimulation leads or electrodes. None of these electrochemical methods are known to have been applied to bioelectrical stimulation leads or electrodes for the purpose of increasing the surface area of pacing electrodes. Furthermore, none of these electrochemical methods are known to have been applied to bioelectrical stimulation leads or electrodes for the purpose of reducing the polarization of stimulating electrodes.

The object of the present invention is to provide a method for reducing the polarization of a stimulating lead without the necessity of applying a coating to the electrode. The present invention achieves low polarization by rearranging or roughening, by electrochemical means, the outer platinum layers of an electrode, resulting in a substantially increased microscopic electrode surface area.

What is also desired is a method for reducing the polarization of a stimulating lead which can reduce the polarization of a wide range of existing pacing leads. The method of the present invention may be applied to all existing noble metal-based pacemaker electrodes.

Furthermore, it is desired to reduce the polarization of leads in a simple, relatively fast, simply automated and easily implemented process which may take place on a production floor.

SUMMARY OF THE INVENTION

In accordance with the teachings of the present invention, there is described a method for processing an implantable electrode for use with a bioelectrical stimulation lead. First, the lead is immersed in an electrolyte solution. Any acid, base or salt electrolyte solution is appropriate. The preferential example of possible salt solution for performing this step is sodium sulfate (e.g. 0.5M $Na_2SO_4$ solution with a pH ranging from 5 to 6). While the lead is immersed, two steps are performed, surface enhancement and hydroxide reduction of the electrode surface. Surface enhancement is the procedure of repetitively applying oscillating anodic and cathodic currents to the electrode at a predetermined frequency in the range from 1 hertz to 10 kilohertz. Each of the applied anodic and cathodic current amplitudes have individually predetermined amplitudes in the range from 1 milliampere to several amperes. Hydroxide reduction involves the application of a lower amplitude reducing current to the electrode. The reducing current ranges in amplitude from approximately 1 microampere to approximately 100 milliamperes. Preferably, this method is applied to a platinum or platinum alloy bioelectrical stimulation electrode, although the method is equally applicable to electrodes fabricated from other noble based metals or alloys, for example gold or iridium.

The oscillating current applied to the electrode in the surface enhancement step may be implemented by controlling the current to vary in the form of a square wave, a sinusoid, a triangular wave, a stairstep function or other known manners of oscillating electrical signals. Furthermore, the oscillating current may be interspersed with intervals during which the current is set to a zero level. In another embodiment of the method, instead of controlling the oscillating current during the surface enhancement step, the process may be implemented by controlling the voltage on the electrode in the form of a square wave, a sinusoid, a triangular wave, a stairstep function or other known manners of oscillating electrical signals. Likewise, the oscillating voltage may be interpolated with intervals during which the voltage is set to a zero level.

Similarly, the current during the hydroxide reduction phase can be applied in the form of DC, ramp, square wave or sinusoidal current, for example. Also, the hydroxide reduction phase can be accomplished by controlling the voltage on the electrode, rather than the current.

The oscillating current applied during the surface enhancing step may be either asymmetric or symmetric with respect to both amplitude and duty cycle. Duty cycle is the ratio of the duration of the anodic interval to the duration of the sum of the anodic interval and the cathodic interval for a single full cycle oscillation.

Furthermore, characteristics of the enhanced surface of a lead may vary according to whether physical motion is applied to the electrolyte solution during the surface enhancement step. Physical motion either may or may not be applied to a particular electrode. A preferred method of supplying surface motion is by application of a sonicator.

During the hydroxide reduction phase, the method involves greatly reducing the current applied to the electrode, for example to 125 uA. When the potential across the electrode becomes smaller than a threshold value, the reduction is complete. Alternatively (or additionally), when the change in potential across the electrodes from one sample to the next becomes smaller than a threshold difference value, the reduction is complete.

The method of the present invention may optionally further comprise the step of cleaning the surface of the electrode. This step, if selected, is performed prior to the surface enhancement step. Surface cleaning comprises alternately applying anodic and cathodic square wave currents to the electrode at a predetermined frequency in the range of from 0.01 hertz to 1 hertz and for a duration ranging from 0.5 seconds to 1 hour. The anodic and cathodic current amplitudes are delivered at individually predetermined amplitudes in the range of from 0.1 milliampere to several amperes. The preferred current value for surface cleaning varies depending on factors such as the size of the electrode and the selection of electrolyte solution.

In accordance with an additional aspect of the present invention, there is described a low polarization electrode which is manufactured in the manner of the previously described method.

Therefore, in accordance with the teachings of the present invention, a method is provided for greatly reducing pacing polarization by electrochemically causing the formation of a thick, highly porous platinum hydrous oxide layer on a cathode. The layer is then slowly reduced to platinum while maintaining an increased surface area therein.

This process does not alter the lead characteristics other than to increase the microsurface area of the electrode. The reduced polarization follows from the known inverse relationship between microsurface area and polarization.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

FIG. 2 is a timing diagram illustrating the manner in which an electrical current is applied to an electrode in an optional electrode surface cleaning or "high electro-current cleaning" phase of the method of the present invention;

FIG. 3 is a timing diagram illustrating a preferred electrical current, a square wave, that is applied to the electrode during a "surface enhancement" phase of the method of the present invention;

DETAILED DESCRIPTION OF THE INVENTION

The method of the present invention for reducing pacing polarization of pacing leads may be applied to existing pacing leads or to parts of leads such as cathodes or anode bands. Whether the method is applied to a pacing lead or a part of a lead, the element to which the method is applied will be referred to as "the electrode" hereinafter. The electrode may be in the form or size of any leads or lead parts as are known in the art of bioelectrical stimulation devices such as pacemakers, defibrillators, cardioverters or antitachycardia pacers.

Figure 1:
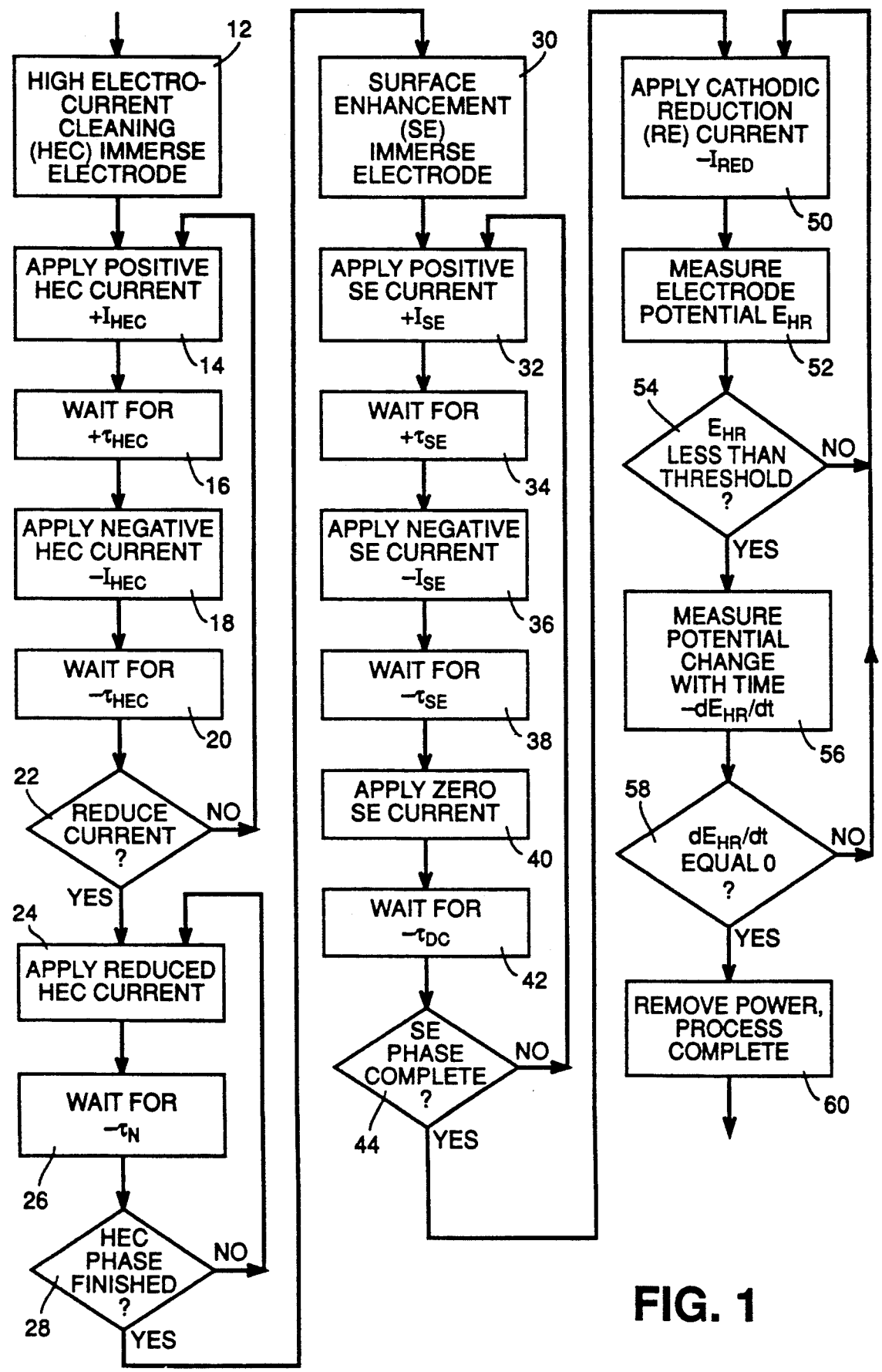
FIG. 1 is a flow diagram, in accordance with the teachings of the present invention, showing the steps of a method for reducing the polarization impedance of a bioelectrical stimulation lead.
Figure 10:
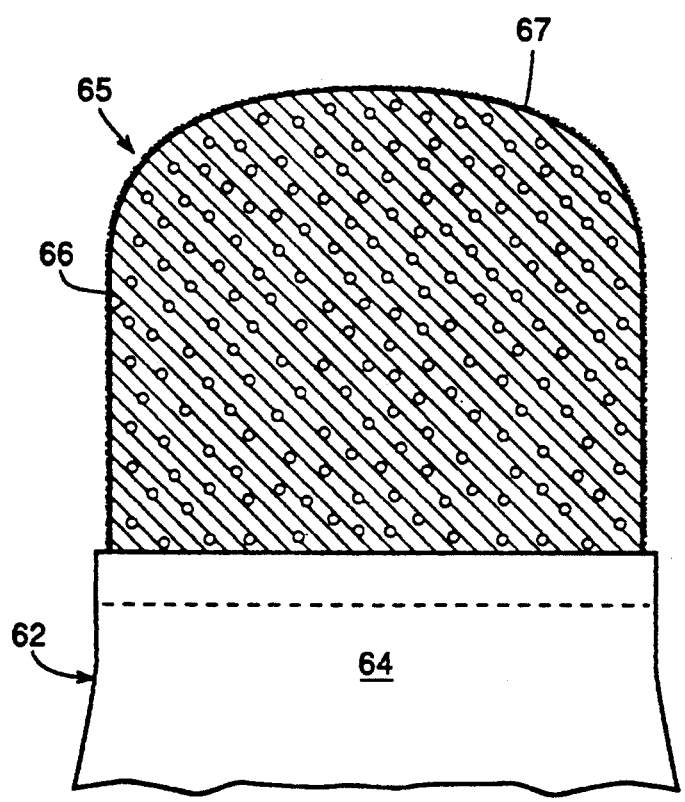
FIG. 10 is a cross-sectional depiction of an end tip assembly of a pacing lead, wherein the electrode portion thereof includes a surface enhanced exterior layer over an electrode conductor.

The preferred embodiment of the method of the present invention comprises three submethods or phases of processing, illustrated in the flow diagram of FIG. 1, which may be applied to a platinum electrode such as the electrode 65 illustrated in FIG. 10. The first phase of the method, comprising blocks 12 through 28, is an optional cleaning procedure, termed "high electro-current cleaning" (HEC), that removes contaminants from the electrode surface. Such contaminants may include epoxy, medical adhesives or primers, fingerprints, grease or dust. The HEC procedure is not required to practice the present invention. A suitable method for lowering the polarization of electrodes and leads may comprise merely those steps of FIG. 1 that follow the HEC procedure.

The HEC procedure is normally performed on both the tip electrode 65 and the anode band (not shown) of a bipolar pacing lead. The first step of the HEC procedure, block 12 of FIG. 1, is to immerse the electrode in an electrolyte solution within a container such as a glass or plastic beaker. Any acid, base or salt electrolyte solution is appropriate. One example of possible salt solution for performing this step is sodium sulfate. After immersing the electrode in the salt solution, a periodic square wave DC current of up to approximately 100 mA is applied to each electrode. The periodic square wave DC current application is performed according to blocks 14 through 22 of FIG. 1, in which a positive current of amplitude $+I_{HEC}$ is applied in block 14 and timed according to the predetermined duration of $+\tau_{HEC}$ in block 16. Likewise, a negative current of amplitude $-I_{HEC}$ is applied in block 18 and timed according to the predetermined duration of $+\tau_{HEC}$ in block 20. Although in the preferred embodiment of the invention the square wave is symmetrical, the magnitude of $+I_{HEC}$ is equal to the magnitude of $-I_{HEC}$, other embodiments of the method may use positive and negative magnitudes of current in different ratios. Furthermore, either the positive or negative $I_{HEC}$ current may be set to the value of zero, thereby allowing the application of only a negative or positive current to the electrode. Also, the order of application of the positive and negative currents may be reversed, thereby transposing the starting and finishing phase of the process.

The preferred embodiment of the invention employs equal time durations of $+\tau_{HEC}$ and $-\tau_{HEC}$, other embodiments of the method may employ negative and positive square wave durations which differ. The applied current waveform produced by the steps of the HEC phase is illustrated in the timing diagram of FIG. 2, in which pulses of 100 mA square wave DC current, $+I_{HEC}$ and $-I_{HEC}$, are applied to the electrode with an alternating polarity and with the polarity changing every 10 sec ($+\tau_{HEC}$ and $-\tau_{HEC}$) for 40 sec. After 40 sec, under the control of a reduce-current logic block 22 of FIG. 1, the applied current is greatly reduced to nearly zero over a 20 sec. period, with the current being reduced in block 24 and the timing function being performed in block 26. The duration of the reduced current step of the HEC procedure is governed by a logic block 28. The entire HEC procedure current may be applied for a reasonable time, under the control of logic blocks 22 and 28 of FIG. 1, ranging from zero seconds to 20 minutes although a preferred duration is approximately one minute. The application of current to the electrode during the HEC submethod creates a charge which is stored on the capacitive elements of the electrode. It is desirable to dissipate this charge before proceeding to the surface enhancement submethod. The reduced-current steps 24 through 28 are provided to hasten the discharge of the charged electrode. However, the reduced-current steps 24 through 28 are optional. Furthermore, the number of steps applied and magnitude of the reduced current are not critical to the success of the overall procedure. If these steps are applied, the final step may be the application of either a positive or negative current to the electrode.

An additional processing step, the application of physical motion to the solution, such as by the application of sonication, may or may not be employed concurrently with the steps of blocks 14 through 28 of FIG. 1. If physical motion is applied, the amount of such motion may be controlled in varying proportions.

Upon completion of the HEC procedure, the electrode may be rinsed with distilled water prior to beginning the second submethod or phase of the polarization reduction method, although this step is not required to perform the process.

The second submethod or phase of the polarization reduction method is surface enhancement. The steps of the surface enhancement phase are shown in blocks 30 through 44 of FIG. 1. The first step of surface enhancement, shown in block 30, is to immerse the electrode, along with a counter-electrode, in a solution within a container, such as a glass or plastic beaker. The container may be submersed in a sonicator. The solution may range in pH from strongly acidic (0) to strongly basic (14), although a pH ranging from 5 to 6 is preferable. The ionic composition of the solution is not critical. In general, all known organic or inorganic acids, salts and bases which have been tested have yielded good results. The preferred solution is sodium sulfate ($Na_2SO_4$). The solution may contain anions like (but not limited to) hydroxides, sulphates, chlorides, perchlotides. Alternatively, the solution may include cations such as (but not limited to) hydrogen, sodium and potassium in combination with organic acids and salts. Likewise, the solution concentration may range from a low molar solution (1 mM) to a high molar solution (10M).

After immersing the electrode in the solution, a periodic square wave DC current of up to approximately 90 mA is applied to the electrode. In the preferred embodiment of the invention, the current waveform is applied in the form of a periodic square-wave. In other embodiments of the invention, the current may be applied in a triangular, staircase, sinusoidal or other waveform.

Furthermore, in the preferred embodiment of the invention, the applied current is controlled to achieve surface enhancement of the electrode. In other embodiments of the invention, an applied voltage may be controlled to provide surface enhancement.

Figure 8:
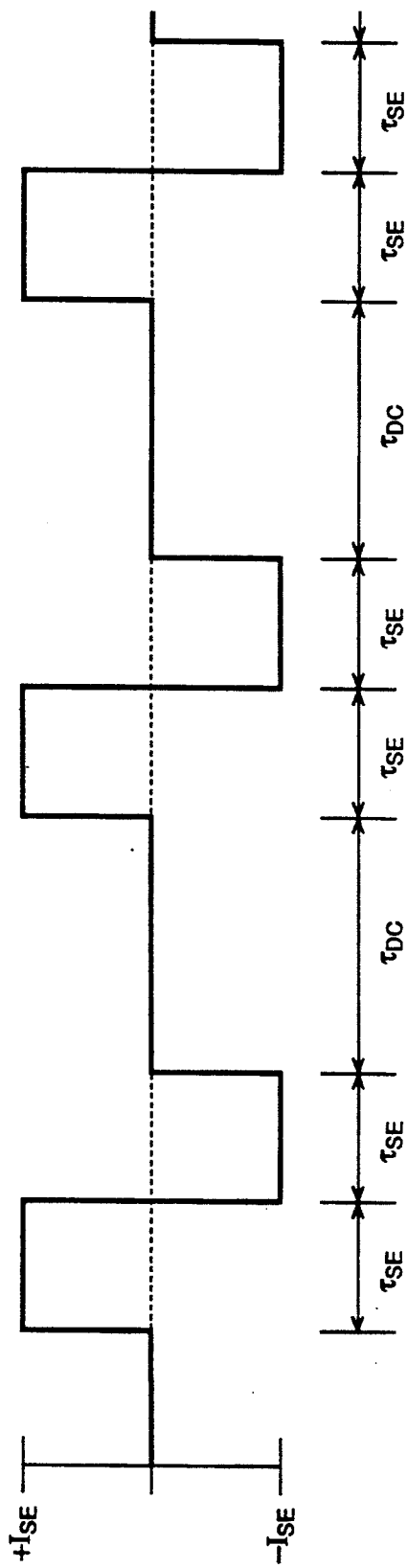
FIG. 8 is a timing diagram illustrating another variation of the treatment parameters for the square wave current of FIG. 3, in which zero amplitude intervals are incorporated into the square wave current.

The periodic square wave DC current application is performed according to blocks 32 through 44 of FIG. 1, in which a positive current of amplitude $+I_{SE}$ is applied in block 32 and timed according to the predetermined duration of $+\tau_{SE}$ in block 34. Likewise, a negative current of amplitude $-I_{SE}$ is applied in block 36 and timed according to the predetermined duration of $+\tau_{SE}$ in block 38. Although in the preferred embodiment of the invention the magnitude of $+I_{SE}$ is equal to the magnitude of $-I_{SE}$, other embodiments of the method may use positive and negative magnitudes of current in different ratios. Likewise, the preferred embodiment of the invention employs symmetrical current pulses, equal time durations of $+\tau_{SE}$ and $-\tau_{SE}$, other embodiments of the method may employ negative and positive square wave durations which differ. A zero current pulse is accomplished by steps 40 and 42 in which the current is reduced to zero in block 40 and the duration of the "off" phase of the applied current is timed in block 42. The applied current waveform produced by the steps of the surface enhancement phase is illustrated in the timing diagram of FIG. 8, in which pulses of 90 mA square wave DC current, $+I_{SE}$ and $-I_{SE}$, are applied to the electrode with an alternating polarity, with the polarity changing approximately every 0.71 ms ($+\tau_{SE}$ and $-\tau_{SE}$) and with a zero amplitude current lasting for approximately 1.44 ms, to achieve an imposed frequency of 350 Hz. Surface enhancement results in the formation of a thick, porous, non-stoichiometric platinum hydroxide layer on the electrode. The periodic square wave DC current may be applied for a reasonable time, governed by logic block 44, ranging from 1 second to 24 hours although a preferred duration for the surface enhancement phase is approximately 7.5 minutes. The current amplitude, frequency, duty cycle, zero current time and total application time for the surface enhancement phase may vary depending on the characteristics of the lead being processed. The range of amplitude for the anodic and cathodic currents ranges from 1 to 500 mA. The appropriate value of applied current depends on the surface area of the electrode prior to processing. A reasonable range of amplitudes for most electrodes ranges from 50 to 250 mA. Furthermore, the amplitude may be symmetric, wherein the positive magnitude may equal the negative magnitude, or the amplitude may be offset by from $-100\%$ to $+100\%$. Best results have been obtained with an offset ranging from 0% to about 2%.

The current is generally applied with an oscillating frequency in the range from 1 Hz to 10 kHz. Most electrodes are best processed with current frequencies in the range from 250 Hz to 1.5 kHz. Duty cycle, the ratio of the duration of the anodic interval to the duration of the sum of the anodic interval and the cathodic interval, is selected in the range of from 1% to 99%. Best results have been obtained using a 50% duty cycle.

Figure 4:
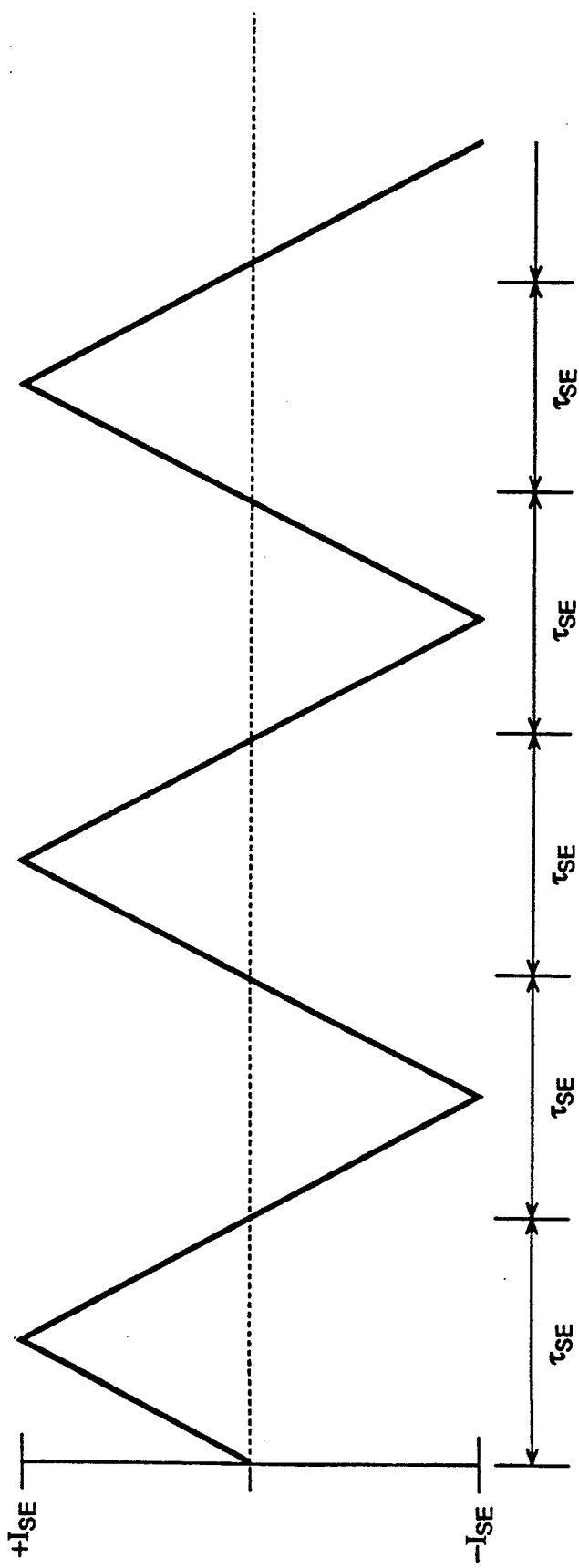
FIG. 4 is a timing diagram which illustrates an alternate electrical current, a triangular wave, that may be applied to the electrode during the "surface enhancement" phase of the method of the present invention.
Figure 5:
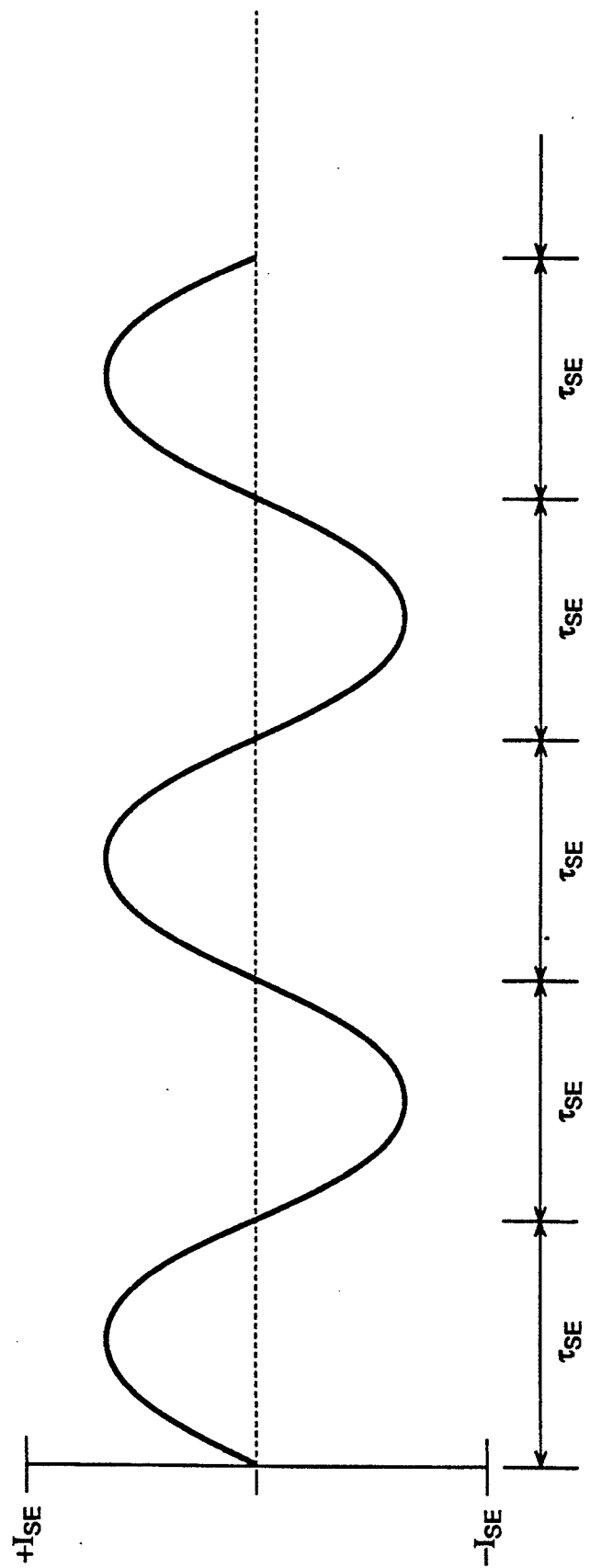
FIG. 5 is a timing diagram illustrating another alternate electrical current, a sinusoidal wave, that may be applied to the electrode during the "surface enhancement" phase of the method of the present invention.
Figure 6:
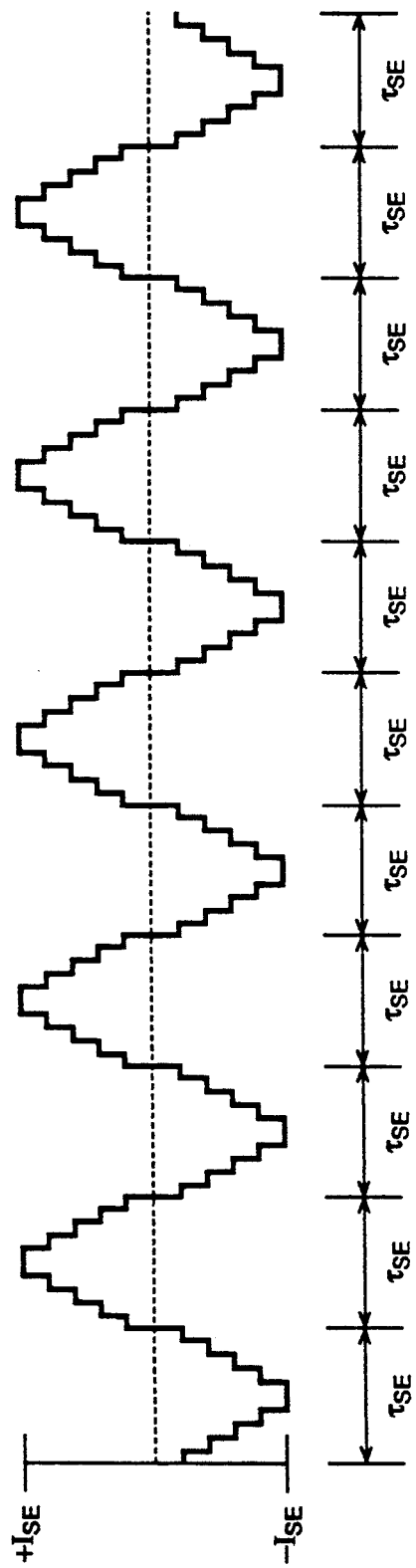
FIG. 6 is a timing diagram illustrating, yet another electrical current, a staircase wave, that may be applied to the electrode during the "surface enhancement" phase of the method of the present invention.
Figure 7:
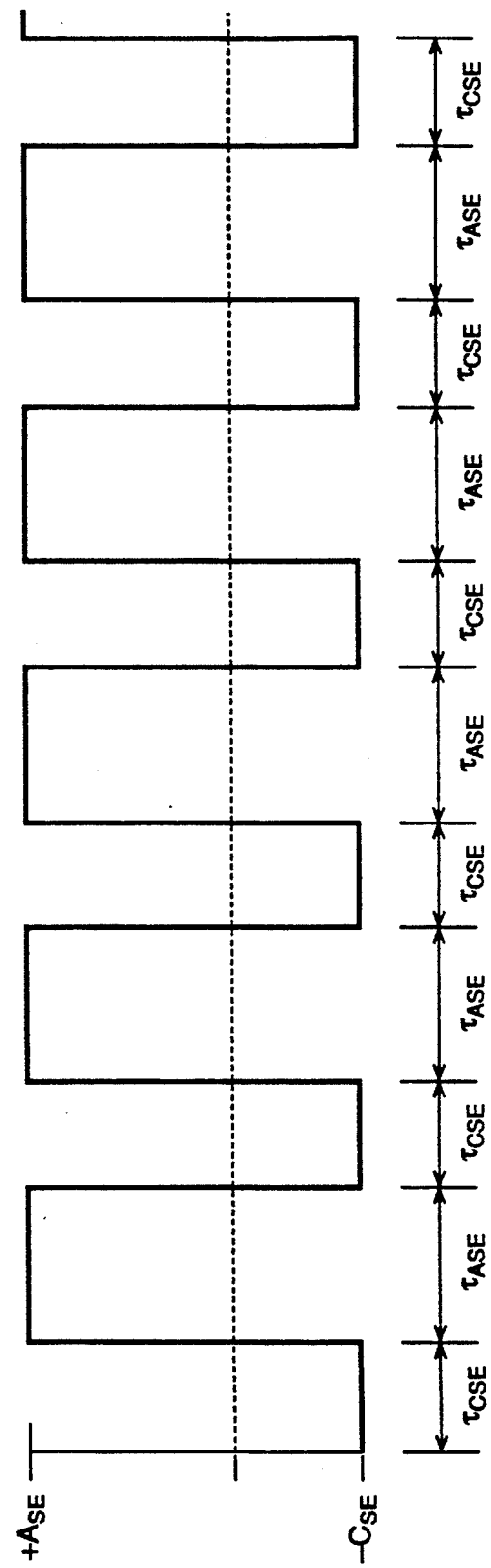
FIG. 7 is a timing diagram illustrating a variation of the treatment parameters for the square wave current of FIG. 3, in which the amplitude and duty cycle are made asymmetric rather than symmetric.

An additional processing step, the application of physical motion to the solution such as by the application of sonication, may or may not be applied to the electrode concurrently with the operations of blocks 32 through 44 of FIG. 1. If physical motion is applied, the amount of motion may be controlled in varying proportions. The preferred embodiment of the invention employs a current waveform, which is applied in the form of a periodic square-wave depicted in FIG. 3. In other embodiments of the invention, the current may be applied in a square wave interrupted by intervals of zero current (FIG. 8), triangular wave (FIG. 4), sinusoidal wave (FIG. 5), staircase wave (FIG. 6) or other form. The waveform of FIG. 7 illustrates an applied current in the form of a square wave having an asymmetric current magnitude, in which an anodic current amplitude $+A_{SE}$ is different from a cathodic current amplitude $-C_{SE}$, and an asymmetric duty cycle, in which an anodic current time duration $\tau_{ASE}$ is different from a cathodic current time duration $\tau_{CSE}$.

After the surface enhancement phase timer under the control of block 44 of FIG. 1 expires, the third phase of the method may begin. The third submethod or phase of the polarization reduction method is an hydroxide reduction phase to slowly reduce the platinum hydroxide layer to platinum, while maintaining an increased surface area structure on the electrode. The steps of the hydroxide reduction phase of the method are illustrated in blocks 50 through 60 of FIG. 1. The slow reduction of platinum hydroxide preserves the porous structure gained during the surface enhancement phase, resulting in a pure platinum surface with a significantly increased surface area. To accomplish reduction, a low amplitude DC current is applied to the electrode in apply-cathodic-reduction-(RE)-current block 50. Reduction currents ranging from 1 uA to 100 mA may be applied during block 50 of the hydroxide reduction stage. Currents of about 50 uA to approximately 500 uA are expected to best achieve hydroxide reduction. Although the application of a DC current is employed to best achieve hydroxide reduction, varying or oscillating currents in the form of ramps, cycles, staircases, sinusoids or other forms also will also lead to reduction.

Figure 9:
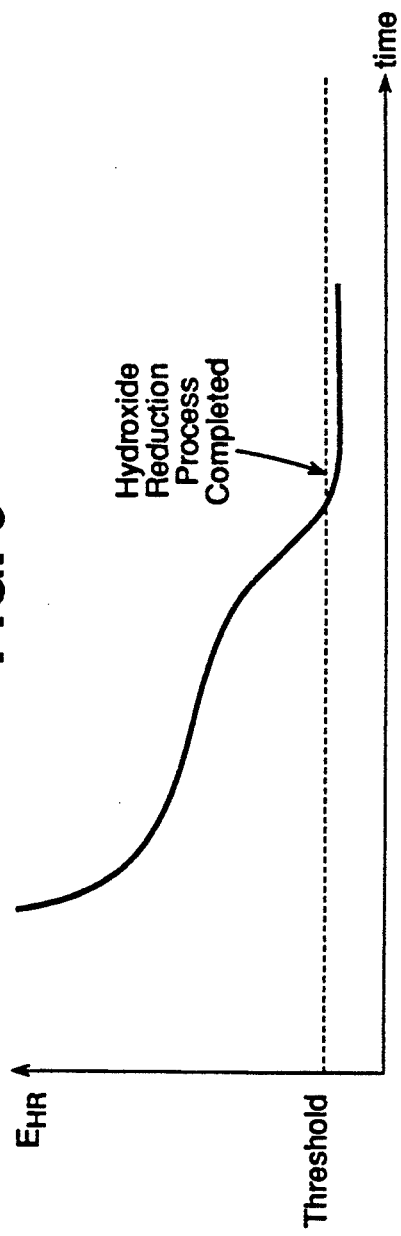
FIG. 9 is a graph showing the reduction in potential with time which occurs in response to the application of a constant current as the hydroxide reduction process proceeds to completion.

While the reduction current is applied during performance of block 50, the potential $E_{HR}$ across the electrode is measured to determine when hydroxide reduction is complete in block 52 of FIG. 1. The graph of FIG. 9 illustrates an expected change in potential $E_{HR}$ as hydroxide reduction takes place. When the reduction process is complete, as is tested according to either or both the magnitude of $E_{HR}$ and the rate at which $E_{HR}$ is changing, the method is complete and terminated according to step 60 of FIG. 1. In the preferred embodiment of the invention, a predetermined threshold level of $E_{HR}$ is compared to the measured value. If the measured $E_{HR}$ value is less than the threshold value, according to the test and logic operation of $E_{HR}$-less-than-threshold block 54 then the change in cell potential over time is determined in measure-potential-change-with-time-$dE_{HR}$/dt block 56. Otherwise, the cathodic reduction current continues to be applied to the electrode in apply-cathodic-reduction-(RE)-current block 50.

Block 56 measures the rate of change of $E_{HR}$ over time and compares the result to a second predetermined threshold level corresponding to the derivative of $E_{HR}$ in time. If the measured $E_{HR}$/dt value is less than the threshold value, according to the test and logic operation of $dE_{HR}$/dt-equal-O logic block 58, then the process is complete. Therefore, when the rate of change of $E_{HR}$ over time is reduced to zero, then the polarization reduction method is complete. Otherwise, the cathodic reduction current continues to be applied to the electrode in apply-cathodic-reduction-(RE)-current block 50. When the rate of change of $E_{HR}$ over time is reduced to zero, remove-power,process-complete block 60 terminates power to the electrode.

Although the process as described above employs one surface enhancement step and one hydroxide reduction step, good results are also obtained using a multiple sequence of enhancement and reduction steps.

FIG. 10, which is a cross-sectional depiction of an end tip assembly of a pacing lead 62, illustrates a tip member or electrode 65 after processing using the surface enhancement method of this invention. An elongated conductor (not shown), within a lead 62 and covered by a layer of insulation 64, is securely attached to tip electrode 65 in any suitable known manner so that electrical impulses from the conductor will be imparted to the tip electrode 65 as necessary. The electrode 65 includes a shaped, porous, platinum substrate 66 that underlies and gives shape to a surface enhanced outer layer 67, which surface enhanced outer layer 67 is formed by the present process that includes surface enhancement and hydroxide reduction as discussed with respect to FIG. 1.

From the foregoing discussion, it will be apparent that the present invention provides a simple and effective method for reducing the polarization impedance of bioelectrical stimulation electrodes and leads which does not require the application of special coatings or etching processes. This method may be applied to various types and configurations of electrodes and leads in a simple, quick and efficient step in the manufacturing process. Many different electrode materials (for example, platinum, titanium, gold, iridium and other metals and alloys) can be treated according to this method.

Although the invention has been described with reference to a particular embodiment, it is to be understood that this embodiment is merely illustrative of the application of the principles of the invention. Numerous modifications may be made therein and other arrangements may be devised without departing from the true spirit and scope of the invention.

What is claimed is:

1. A method for manufacturing a metallic electrode of an implantable lead for generating bioelectrical stimulation pulses and sensing bioelectrical signals, comprising the steps of:

immersing the electrode in an electrolyte solution;
   enhancing the surface of the immersed electrode by repetitively applying oscillating anodic and cathodic current pulses to the electrode at a set frequency in the range of from 1 hertz to 10 kilohertz, said anodic and cathodic current pulses each having a set amplitude in the range of from 1 milliampere to several amperes, so that a porous metallic hydrous oxide layer is formed on the surface of the immersed electrode; and
   reducing the hydroxide on the surface of the immersed electrode by applying lower amplitudes reducing current pulses to the electrode, the reducing current pulses each having a set amplitude in the range of from approximately 1 microampere to approximately 100 milliamperes.

2. A method in accordance with claim 1, wherein the oscillating current pulses applied during said surface enhancing step are applied as a waveform, said waveform selected from the group consisting of square wave varying currents, sinusoidally varying currents, triangular wave varying currents and staircase varying currents.

3. A method in accordance with claim 2, wherein the oscillating current pulses applied during said surface enhancing step are periodically suspended by zero current intervals having a preset timing and duration.

4. A method in accordance with claim 1, wherein the oscillating current pulses applied during said surface enhancing step are generated by controlling the voltage output waveform, said waveform selected from the group of consisting of square wave varying voltages, sinusoidally varying voltages, triangular wave varying voltages and staircase varying voltages.

5. A method in accordance with claim 4, wherein the oscillating current pulses applied during said surface enhancing step are periodically suspended by zero current intervals having a preset timing and duration.

6. A method in accordance with claim 1, wherein said anodic and cathodic current pulses each have individually set amplitudes, and wherein the oscillating current pulses applied during said surface enhancing step are asymmetric with respect to amplitude.

7. A method in accordance with claim 1, wherein said anodic and cathodic current pulses each have individually set amplitudes, and wherein the oscillating current pulses applied during said surface enhancing step are symmetric with respect to amplitude.

8. A method in accordance with claim 2, wherein said anodic and cathodic current pulses each have individually set amplitudes, and wherein the oscillating current pulses applied during said surface enhancing step are symmetric with respect to amplitude.

9. A method in accordance with claim 1, wherein said anodic and cathodic current pulses each have individually set amplitudes, and wherein the oscillating current pulses applied during said surface enhancing step are asymmetric with respect to duty cycle.

10. A method in accordance with claim 1, wherein said anodic and cathodic current pulses each have individually set amplitudes, and wherein the oscillating current pulses applied during said surface enhancing step are symmetric with respect to duty cycle.

11. A method in accordance with claim 8, wherein the oscillating current pulses applied during said surface enhancing step are symmetric with respect to duty cycle.

12. A method in accordance with claim 1, wherein said surface enhancing step further comprises the step of applying physical motion to the electrolyte solution.

13. A method in accordance with claim 12, wherein said physical motion applying step is performed by activating a sonicator.

14. A method in accordance with claim 11, wherein said surface enhancing step further comprises the step of applying physical motion to the electrolyte solution.

15. A method in accordance with claim 14, wherein said physical motion applying step is performed by activating a sonicator.

16. A method in accordance with claim 1, wherein said surface enhancing step is performed for a set duration in the range from 10 seconds to 72 hours.

17. A method in accordance with claim 15, wherein said surface enhancing step is performed for a set duration in the range from 10 seconds to 72 hours.

18. A method for manufacturing a metallic electrode of an implantable lead for generating bioelectrical stimulation pulses and sensing bioelectrical signals, comprising the steps of:

immersing the electrode in an electrolyte solution;

enhancing the surface of the immersed electrode by repetitively applying oscillating anodic and cathodic currents to the electrode at a set frequency in the range of from 1 hertz to 10 kilohertz, said anodic and cathodic currents each having amplitudes in the range of from 1 milliampere to several amperes, so that a porous metallic hydrous oxide layer is formed on the surface of the immersed electrode; and reducing the hydroxide on the surface of the immersed electrode by applying lower amplitudes reducing current to the electrode, the reducing current having a set amplitude in the range of from approximately 1 microampere to approximately 100 milliamperes, said hydroxide reduction current being a DC current, said hydroxide reduction step further comprising the substeps of:

repetitively measuring the voltage across the immersed electrode resulting from the applied hydroxide reduction current; and terminating said hydroxide reduction step when the measured voltage falls below a set threshold voltage.

19. A method for manufacturing a metallic electrode of an implantable lead for generating bioelectrical stimulation pulses and sensing bioelectrical signals, comprising the steps of:

immersing the electrode in an electrolyte solution;

enhancing the surface of the immersed electrode by repetitively applying oscillating anodic and cathodic currents to the electrode at a set frequency in the range of from 1 hertz to 10 kilohertz, said anodic and cathodic currents each having amplitudes in the range of from 1 milliampere to several amperes, so that a porous metallic hydrous oxide layer is formed on the surface of the immersed electrode; and reducing the hydroxide on the surface of the immersed electrode by applying lower amplitude reducing current to the electrode, the reducing current having a set amplitude in the range of from approximately 1 microampere to approximately 100 milliamperes, said hydroxide reduction current being a DC current, said hydroxide reduction step further comprising the substeps of:

repetitively measuring the voltage across the immersed electrode resulting from the applied hydroxide reduction current;

determining the rate of change of the measured voltage with respect to time; and terminating said hydroxide reduction step when the rate of change of the measured voltage with respect to time falls below a set threshold.

20. A method for manufacturing a metallic electrode of an implantable lead for generating bioelectrical stimulation pulses and sensing bioelectrical signals, comprising the steps of:

immersing the electrode in an electrolyte solution;

enhancing the surface of the immersed electrode by repetitively applying oscillating anodic and cathodic currents to the electrode at a set frequency in the range of from 1 hertz to 10 kilohertz, said oscillating currents being applied as a waveform, said waveform selected from the group consisting of square wave varying currents, sinusoidally varying currents, triangular wave varying currents and staircase varying currents, said anodic and cathodic currents each having individually set amplitudes, said oscillating currents being symmetric with respect to amplitude, said oscillating currents being symmetric with respect to duty cycle, said surface enhancing step further comprising the step of applying physical motion to the electrolyte solution, said physical motion applying step being performed by activating a sonicator, said surface enhancing step being performed for a set duration in the range of from 10 seconds to 72 hours, said anodic and cathodic currents each having amplitudes in the range of from 1 milliampere to several amperes, so that a porous metallic hydrous oxide layer is formed on the surface of the immersed electrode; and reducing the hydroxide on the surface of the immersed electrode by applying a lower amplitude reducing current to the electrode, the reducing current having a set amplitude in the range of from approximately 1 microampere to approximately 100 milliamperes, said hydroxide reduction current being a DC current, and said hydroxide reduction step further comprising the substeps of:

repetitively measuring the voltage across the immersed electrode resulting from the applied hydroxide reduction current; and terminating said hydroxide reduction step when the measured voltage falls below a set threshold voltage.

21. A method for manufacturing a metallic electrode of an implantable lead for generating bioelectrical stimulation pulses and sensing bioelectrical signals, comprising the steps of:

immersing the electrode in an electrolyte solution;
enhancing the surface of the immersed electrode by repetitively applying oscillating anodic and cathodic currents to the electrode at a set frequency in the range of from 1 hertz to 10 kilohertz, said oscillating currents being applied as a waveform, said waveform selected from the group consisting of square wave varying currents, sinusoidally varying currents, triangular wave varying currents and staircase varying currents, said anodic and cathodic currents each having individually predetermined amplitudes, said oscillating currents being symmetric with respect to amplitude, said oscillating currents being symmetric with respect to duty cycle, said surface enhancing step further comprising the step of applying physical motion to the electrolyte solution, said physical motion applying step being performed by activating a sonicator, said surface enhancing step being performed for a set duration in the range from 10 seconds to 72 hours, said anodic and cathodic currents each having amplitudes in the range of from 1 milliampere to several amperes, so that a porous metallic hydrous oxide layer is formed on the surface of the immersed electrode; and reducing the hydroxide on the surface of the immersed electrode by applying a lower amplitude reducing current to the electrode, the reducing current having a set amplitude in the range of from approximately 1 microampere to approximately 100 milliamperes, said hydroxide reduction current being a DC current, and said hydroxide reduction step further comprising the substeps of:

repetitively measuring the voltage across the immersed electrode resulting from the applied hydroxide reduction current;

determining the rate of change of the measured voltage with respect to time; and terminating said hydroxide reduction step when the rate of change of the measured voltage with respect to time falls below a set threshold.

22. A method in accordance with claim 20, wherein the electrolyte solution is approximately 0.5 Molar $Na_2SO_4$ having a pH ranging from 5 to 6 and said surface enhancing step applies square wave anodic and cathodic currents to the electrode, said currents having an oscillating current frequency of approximately 350 Hz, said anodic current having an amplitude of approximately 90 mA and said cathodic current having an amplitude of approximately 90 mA, said surface enhancing step being applied for approximately 7.5 minutes.

23. A method for manufacturing a metallic electrode of an implantable lead for generating bioelectrical stimulation pulses and sensing bioelectrical signals, comprising the steps of:

immersing the electrode in an electrolyte solution, said electrolyte solution being approximately 0.5 Molar $Na_2SO_4$ having a pH ranging from 5 to 6;

enhancing the surface of the immersed electrode by repetitively applying oscillating anodic and cathodic currents to the electrode at a set frequency in the range of from 1 hertz to 10 kilohertz, said oscillating currents being applied as a waveform, said waveform selected from the group consisting of square wave varying currents, sinusoidally varying currents, triangular wave varying currents and staircase varying currents, said anodic and cathodic currents each having individually set amplitudes, said oscillating currents being symmetric with respect to amplitude, said oscillating currents being symmetric with respect to duty cycle, said surface enhancing step applying square wave anodic and cathodic currents to the electrode, said currents having an oscillating current frequency of approximately 1000 Hz, said anodic current having an amplitude of approximately 91 mA and said cathodic current having an amplitude of approximately 87 mA, said surface enhancing step being applied for approximately 7.5 minutes.

24. A method for manufacturing a metallic electrode of an implantable lead for generating bioelectrical stimulation pulses and sensing bioelectrical signals, comprising the steps of:

immersing the electrode in a first electrolyte solution;
cleaning the surface of said immersed electrode by alternately applying anodic and cathodic square wave currents to the electrode at a set frequency in the range of from 0.01 hertz to 1 hertz and for a duration ranging from 0.5 seconds to 1 hour, said anodic and cathodic currents each having amplitudes in the range of from 1 milliampere to 1 ampere;

immersing the electrode in a second electrolyte solution;

enhancing the surface of said electrode in said second solution by repetitively applying oscillating anodic and cathodic currents to the electrode at a set frequency in the range of from 1 hertz to 10 kilohertz, said anodic and cathodic currents each having amplitudes in the range of from 1 milliampere to several amperes, so that a porous metallic hydrous oxide layer is formed on the surface of the immersed electrode; and reducing the hydroxide on the surface of said electrode in said second solution by applying a lower amplitude reducing current to the electrode, the reducing current having a set amplitude in the range of from approximately 1 microampere to approximately 100 milliamperes.

25. A method in accordance with claim 24, further comprising the step, following a last cycle of said surface cleaning step, of reducing the applied current from the current applied during the final surface cleaning step cycle to zero in a stairstep manner.

26. An electrode of an implantable lead for generating bioelectrical stimulation pulses and sensing bioelectrical signals, comprising:
a noble metal conductor substrate; and
a noble metal, porous, conductive low impedance surface layer overlying said conductive substrate, said surface layer having been formed by immersing the conductive substrate in an electrolyte solution, enhancing the surface of the immersed substrate by repetitively applying oscillating anodic and cathodic current pulses to the substrate at a set frequency in the range of from 1 hertz to 10 kilohertz, said anodic and cathodic current pulses each having a set amplitude in the range of from 1 milliampere to several amperes, and reducing the hydroxide on the surface of the immersed substrate by applying lower amplitude reducing current pulses to the substrate, said reducing current pulses each having an amplitude in the range of approximately 1 microampere to approximately 100 milliamperes.

27. An electrode in accordance with claim 26, wherein said low impedance surface layer is enhanced by applying the oscillating anodic and cathodic current pulses as a waveform, said waveform selected from the group consisting of square wave varying currents, sinusoidally varying currents, triangular wave varying currents and staircase varying currents.

28. An electrode in accordance with claim 27, wherein said anodic and cathode current pulses each have individually set amplitudes, and wherein said low impedance surface layer is enhanced by applying the oscillating anodic and cathodic current pulses as a symmetric waveform with respect to amplitude.

29. An electrode in accordance with claim 28, wherein the duty cycle of said oscillating anodic and cathodic current pulses is symmetrical.

30. An electrode in accordance with claim 29, wherein said low impedance surface layer is enhanced by applying physical motion to the electrolyte solution while said oscillating anodic and cathodic current pulses are being applied.

31. An electrode in accordance with claim 30, wherein said physical motion is generated by a sonicator.

* * * * *